(12) United States Patent
Deng et al.

(10) Patent No.: US 10,971,250 B2
(45) Date of Patent: Apr. 6, 2021

(54) DYNAMIC AND ACCRETIVE COMPOSITION OF PATIENT ENGAGEMENT INSTRUMENTS FOR PERSONALIZED PLAN GENERATION

(71) Applicant: International Business Machines Corporation, Armonk, NY (US)

(72) Inventors: Vincent Deng, Jhongli (TW); Pei-Yun Hsueh, New York, NY (US); Sreeram Ramakrishnan, Yorktown Heights, NY (US); Xinxin Zhu, Croton on Hudson, NY (US)

(73) Assignee: International Business Machines Corporation, Armonk, NY (US)

( * ) Notice: Subject to any disclaimer, the term of this patent is extended or adjusted under 35 U.S.C. 154(b) by 894 days.

(21) Appl. No.: 14/716,267

(22) Filed: May 19, 2015

(65) Prior Publication Data
US 2016/0342771 A1 Nov. 24, 2016

(51) Int. Cl.
| | | |
|---|---|---|
| G16H 10/20 | (2018.01) | |
| G16H 10/60 | (2018.01) | |
| G16H 20/30 | (2018.01) | |
| G16H 70/20 | (2018.01) | |
| G09B 23/28 | (2006.01) | |
| G09B 7/00 | (2006.01) | |
| G09B 19/00 | (2006.01) | |

(52) U.S. Cl.
CPC ............ *G16H 10/20* (2018.01); *G09B 7/00* (2013.01); *G09B 19/00* (2013.01); *G09B 23/28* (2013.01); *G16H 10/60* (2018.01); *G16H 20/30* (2018.01); *G16H 70/20* (2018.01)

(58) Field of Classification Search
CPC ............................ G06Q 50/24; G06F 19/3418
USPC .......................................................... 705/2–3
See application file for complete search history.

(56) References Cited

U.S. PATENT DOCUMENTS

| | | |
|---|---|---|
| 5,657,256 A | 8/1997 | Swanson et al. |
| 7,165,012 B2 | 1/2007 | Swanson |
| | (Continued) | |

FOREIGN PATENT DOCUMENTS

| | | |
|---|---|---|
| WO | 2004061744 A2 | 7/2004 |
| WO | 2005081119 A2 | 9/2005 |
| | (Continued) | |

OTHER PUBLICATIONS

Ware, J.E. et al., "Practical Implications of Item Response Theory and Computerized Adaptive Testing: A Brief Summary of Ongoing Studies of Widely Used Headache Impact Scales" Medical Care (Sep. 2000) pp. II-73-II-82, vol. 38, No. 9, Supplment II.

(Continued)

*Primary Examiner* — John P Go
(74) *Attorney, Agent, or Firm* — Scully, Scott, Murphy & Presser, P.C.; Kristofer L. Haggerty, Esq.

(57) ABSTRACT

Instruments of determined level of self-efficacy may be chosen dynamically for customized patient engagement, e.g., based on a patient's latent adherence trait estimated from lifestyle and other clinical data. Customization points in care plans may be identified, e.g., by monitoring an accumulative change in the patient's health literacy level. Clinical decision support at the point of care may be provided by adjusting patient engagement strategies and allocating resources accordingly.

13 Claims, 6 Drawing Sheets

(56) References Cited

U.S. PATENT DOCUMENTS

| | | | |
|---|---|---|---|
| 2004/0010420 A1* | 1/2004 | Rooks | G06F 19/3481 705/2 |
| 2005/0187436 A1* | 8/2005 | Doniger | A61B 5/16 600/300 |
| 2008/0268412 A1 | 10/2008 | Mulcahy et al. | |
| 2012/0129139 A1 | 5/2012 | Partovi | |
| 2012/0191469 A1* | 7/2012 | Akradi | G06Q 50/22 705/2 |
| 2012/0232931 A1* | 9/2012 | Buisman | G06F 19/3418 705/3 |
| 2013/0325505 A1 | 5/2013 | Vengco | |
| 2013/0304493 A1 | 11/2013 | Partovi | |
| 2014/0122109 A1 | 1/2014 | Ghanbari et al. | |
| 2014/0186811 A1 | 3/2014 | Lemke et al. | |

FOREIGN PATENT DOCUMENTS

| | | | | |
|---|---|---|---|---|
| WO | 2006026641 A1 | 3/2006 | | |
| WO | WO-2007027837 A2 * | 3/2007 | | G16H 15/00 |
| WO | 2007066287 A2 | 6/2007 | | |
| WO | 2008102279 A1 | 8/2008 | | |
| WO | 2011103495 A2 | 8/2011 | | |
| WO | 2014164863 A1 | 10/2014 | | |

OTHER PUBLICATIONS

Mohebi, S. et al., "Review the key role of self-efficacy in diabetes care " J Educ Health Promot (Jul. 2013) pp. 1-7, vol. 2.

Mulcahy, K. et al., "Diabetes Self-Management Education Core Outcomes Measures" The Diabetes Educator (Sep./Oct. 2003) pp. 768-803, vol. 29, No. 5.

Lansky, D., "Patient Engagement and Patient Decision-making in US Health Care" FACCT—Foundation for Accountability (Jul. 11-13, 2003) pp. 1-13.

Young, D. et al, "Patient Engagement and Coaching for Health: The PEACH study—a cluster randomized controlled trial using the telephone to coach people with type 2 diabetes to engage with their GPs to improve diabetes care: a study protocol" BMC Family Practice (Apr. 2007) pp. 1-9, vol. 8, No. 20.

Prochaska, J.O. et al., "Standardized, Individualized, Interactive, and Personalized Self-Help Programs for Smoking Cessation" Health Psychology (Sep. 1993) pp. 399-405, vol. 12, No. 5.

List of IBM Patents or Patent Applications Treated as Related, dated Nov. 2, 2017, 2 pages.

Office Action dated Oct. 5, 2017 received in U.S. Appl. No. 14/748,740, 15 pages.

Office Action dated May 3, 2017 received in U.S. Appl. No. 14/748,740, 14 pages.

Hsueh, P.-Y. S., et al., "Dynamic and Accretive Composition of Patient Engagement Instruments for Personalized Plan Generation", Nursing Informatics 2014, Jun. 21-25, 2014, pp. 447-451.

Office Action dated Jul. 10, 2020 received in U.S. Appl. No. 14/748,740, 16 pages.

Notice of Allowance dated Sep. 29, 2020 received in U.S. Appl. No. 14/748,840, 13 pages.

* cited by examiner

DYNAMIC AND ACCRETIVE COMPOSITION OF PATIENT ENGAGEMENT INSTRUMENTS FOR PERSONALIZED PLAN GENERATION

FIELD

The present application relates generally to computers and computer applications, and more particularly to a dynamic and accretive instrument composition system for health care transformation.

BACKGROUND

Patient engagement helps patients become more informed and active in managing their personal health, and demands effective engagement measurements of patient self-efficacy and capability in various care dimensions. For example, in Diabetes Mellitus (DM) self-management, the American Association of Diabetes Educators (AADE) has defined seven care dimensions that are important for monitoring the progress of self-management behavior: particularly, physical activity, healthy eating, medication taking, monitoring blood glucose, diabetes self-care related problem solving, reducing risks of acute and chronic complications, and psychosocial aspects of living with diabetes. Some care dimensions are more critical to certain sub-populations. For diabetic care, younger patients with unhealthy lifestyle but no complications need to adhere to healthier lifestyles; others who gave up self-management due to significant obstacles may benefit from problem solving and health coping education. In current practice, clinical nurse educators rely on standard tests, such as Mini-Nutrition Assessment (MNA) and the graphic card-based STENO tool, to determine patient self-efficacy in the different care dimensions and to generate patient engagement plans.

In the existing static instrument approaches, the often-lengthy assessment questionnaires cast substantial burden on both patients and clinicians, which could take much of the consultation time during clinical on-site visits. The static instruments also do not differentiate users with different needs. FIG. 5 illustrates an individualized engagement plan for a patient who is exposed to a multitude of co-morbid conditions but has different literacy levels across three different care dimensions—medication, exercise, and diet. While some individual diabetic needs are beginning to be addressed in guidelines, many others remain to be handled by heuristics. In turn, diabetic educators are often placed in a position of choosing education materials for individual patients intuitively. Using the static instruments, patient engagement plans are generated based on "one shot" understanding of patients at the time of initial assessment. The one shot understanding has rendered it difficult to answer questions that require temporal analysis of patient self-efficacy. For example, how is this patient's literacy level on healthy eating changing over time? What assessment items should be brought up in the next clinical encounter? What education materials to brief and what interventions to include in the follow-up stage? In the field of adherence research, a few theoretical constructs, e.g., Transtheoretical Model of Behavior Change (TTM), have been proposed to conceptualize the changes in patient self-efficacy as a progression through a series of stages: particularly, pre-contemplation, contemplation, preparation, action, and maintenance. However, no existing instruments used in current practice have accounted for either the dynamic change of patient self-efficacy or its abstraction in its design.

BRIEF SUMMARY

A method of selecting patient engagement instruments for individualized care, in one aspect, may comprise retrieving a patient's data from a patient database stored in a memory device. The method may also include classifying the patient's condition based on the patient's data into a care dimension category. The method may further include selecting a set of initial instrument items associated with an initially determined level of self-efficacy based on the classifying. The method may also include receiving responses associated with the one or more initial instrument items from the patient. The method may further include receiving medical results of lab tests performed associated with the patient. The method may also include synthesizing and analyzing the responses and the medical results. The method may further include determining a self-efficacy measure associated with the patient based on the synthesizing and the analyzing. The method may also include adjusting the initially determined level of self-efficacy to another level according to the self-efficacy measure. The method may further include selecting a next set of instrument items associated with said another level. The method may also include presenting the next set of instrument items to the patient via a graphical user interface.

A system of selecting patient engagement instruments for individualized care, in one aspect, may comprise an analytics engine operable to execute on one or more hardware processors, the analytics engine further operable to retrieve a patient's data from a patient database stored in a memory device, the analytics engine further operable to classify the patient's condition based on the patient's data into a care dimension category. A questionnaire engine may be operable to execute on one or more of the hardware processors, the questionnaire engine further operable to select a set of initial instrument items associated with an initially determined level of self-efficacy based on the care dimension category classified by the analytics engine. A literacy application module may be operable to execute on the one or more hardware processor and further operable to invoke the analytics engine and the questionnaire engine, and further operable to receive responses associated with the one or more initial instrument items from the patient. The analytics engine may be further operable to receive medical results of lab tests performed associated with the patient. The analytics engine may be further operable to synthesize and analyze the responses and the medical results, the analytics engine further operable to determine a self-efficacy measure associated with the patient based on the synthesizing and the analyzing. The analytics engine may be further operable to adjust the initially determined level of self-efficacy to another level according to the self-efficacy measure. The questionnaire engine may be further operable to select a next set of instrument items associated with said another level. The literacy application module may be further operable to present the next set of instrument items to the patient.

A computer readable storage medium storing a program of instructions executable by a machine to perform one or more methods described herein also may be provided.

Further features as well as the structure and operation of various embodiments are described in detail below with

DETAILED DESCRIPTION

Figure 1:
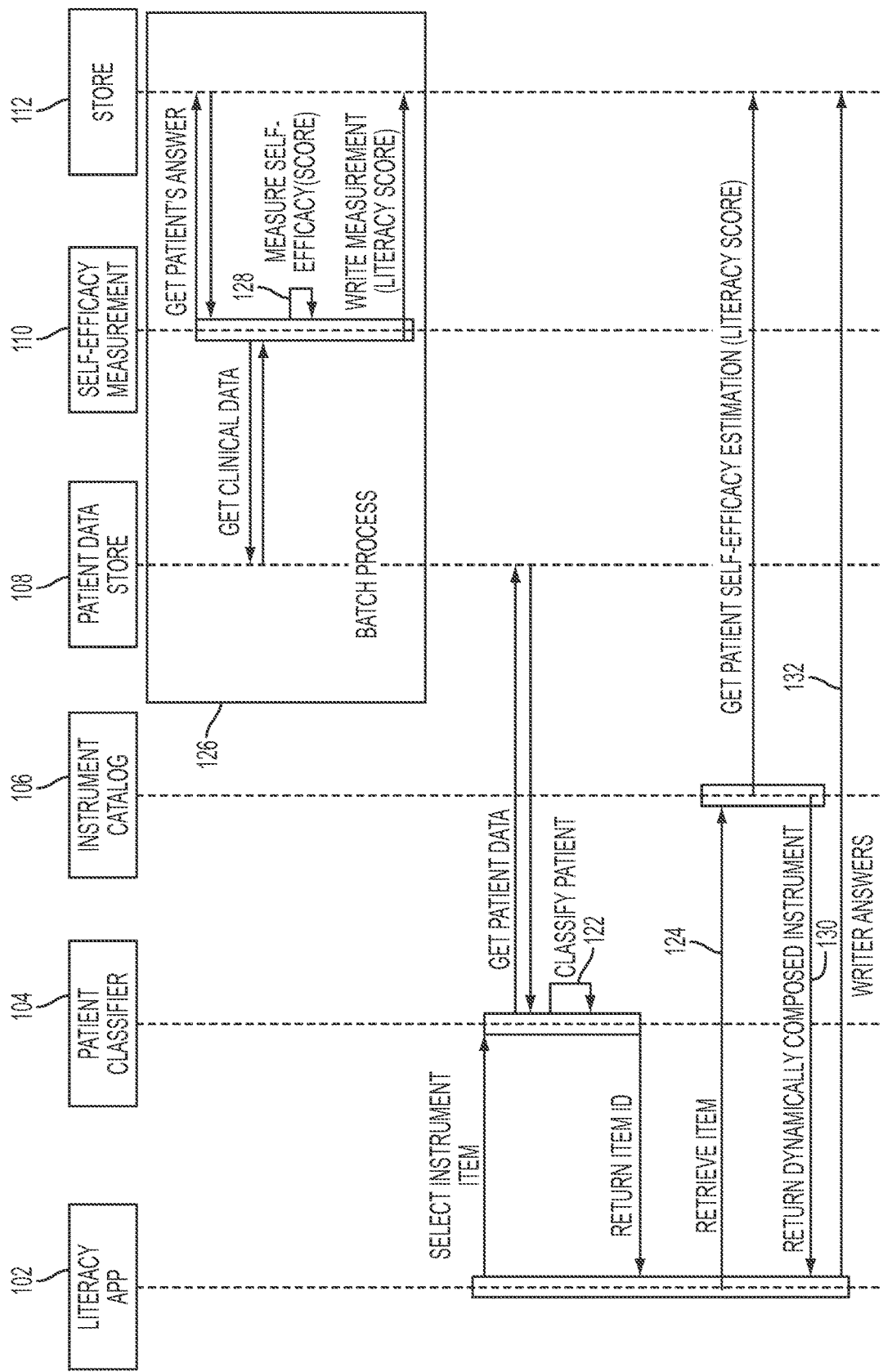
FIG. 1 is a data flowchart illustrating access points in a DAIC-enhanced patient engagement care flow in one embodiment of the present disclosure.

Patient engagement sustains participation in managing patients' health by fostering their self-efficacy to the level necessary to achieve well-being. This means that healthcare delivery systems need to measure the current level of self-efficacy in the different care dimensions. While various questionnaires and test batteries have been devised to help assess self-efficacy, e.g., capability or motivation, they may be insufficient to satisfy the requirements of health self-efficacy assessment, for example, due to the fact that health self-efficacy is not a one-time test, and previous methods lack considerations of changes of human ability over the course of health education.

A dynamic and accretive instrument composition (DAIC) system and methodology are presented that in one embodiment can estimate patient self-efficacy, assess its temporal changes in different care dimensions over time, and iteratively select critical care dimensions and assessment questions to be included in a personalized instrument. In one embodiment, the system and methodology tightly integrate clinical workflow and standard care processes.

Analytics in one embodiment of the present disclosure may facilitate the dynamic composition of such instruments and guide patients through self-management reinforcement cycles. The measurements obtained from the composed instruments can serve as input to disease self-management systems for directing attention to the critical care dimensions and driving the joint decision of follow-up interventions between healthcare professionals and patients at point of care. They can also serve as input to care coordination programs, where multiple service providers collaborate to identify personalization service gaps and provide necessary services for patients with different needs.

A dynamic and accretive instrument composition (DAIC) system and methodology in one embodiment may include hybrid approach, which can leverage not only the existing assessment items that have been curated for many different types of patient engagement scenarios, but also data-driven analytics to model the measurement of patient self-efficacy in various care dimensions. The system-composed patient engagement instrument is integrated into clinical workflow and standard care processes, e.g., by include the following integration points in the care flow: 1) By evaluating patients' educational background, occupations, social, family, and medical histories, demographics, and other baseline information, an algorithm of the present disclosure in one embodiment automatically classifies patients into proper categories so as to generate the most suitable engagement plan. 2) As patients receive health coaching and medical care from clinicians at a given facility, the system monitors the gradual accretion of capability (e.g., health literacy in being physically active) or any surprising changes in the self-efficacy level through patients' responses to help adjust the composition of the next assessment instrument and suggest appropriate intervention. 3) Following the care flow, the system also presents the observed changes in the different care dimensions along with clinical parameters collected from hospital information systems to clinicians at the point of care so that they can revise engagement plans accordingly.

FIG. 1 is a data flowchart illustrating access points in a DAIC-enhanced patient engagement care flow in one embodiment of the present disclosure. Using the methodology, an appropriate instrument may be dynamically chosen for customized patient education delivery. Consider, for example, that Patient A comes for the patient's first health care management appointment, for instance for DM. A literacy application 102 in one embodiment of the present disclosure may retrieve and assess the patient's background information such as education, social and family history, occupation, and historical medical records, for example, from a patient data store 108, then automatically classify the patient (e.g., the patient's condition) to a care dimension category (e.g., category I) shown at 122 (e.g., via a classifier 104), and select the initial health assessment items of the proper level, and for example, retrieves the initial health assessment items via an instrument catalog 106, for example, shown at 124. The initial health assessment items or instrument items are of an initially determined level of self-efficacy, e.g., based on the classifying of the patient or patient's condition. Health assessment items or instrument items refer to questionnaires, health education material/guidelines for patients. The literacy application 102 may receive patient answers or input responding to the initial health assessment items. The answers are input to a batch process 126.

For instance, patient answers questions related to adherence to care plan and engagement with hospital and care providers, filling out optional quiz on personal characteristics. These questions cover multi-dimensional self-care assessment, health behavior awareness, readiness of change, and personal goal at different self-efficacy levels. Lab tests can also be performed to collect baseline medical results, e.g., if the needed information is not readily available in the historical medical records.

The batch process 126 synthesizes and analyzes these answers and baseline medical results. For example, a self-efficacy measurement component 110 dynamically estimates patient current self-efficacy levels (assessment scores), e.g., shown at 128, to select the difficulty level of the next most appropriate assessment and to suggest educational instruments for patient. The self-efficacy measurement component 110 may store the measurements in a data store 112. Based on the measurements, instrument may be dynamically composed using an instrument catalog 106, and the literacy application 102 may present the dynamically composed instrument to the patient as shown at 130, for example, for answers. The answers may be stored in a data store 112, as shown at 132. These answers in turn may be used in the batch process 126 for measuring self-efficacy. For instance, responses from the patient, patient data that may also comprise medical results of lab tests may be synthesized and analyzed to determine a self-efficacy measure associated with the patient. The level of the patient's self-efficacy may be adjusted based on the determined self-efficacy measure, and a next set of instrument items that correspond to the adjusted level of self-efficacy may be selected and presented to the patient.

The process may repeat based on the new set of responses received from the patient with respect to the next set of instrument items. Thus, the patient's self-efficacy level may be iteratively adjusted and a corresponding set of instrument items may be dynamically selected based on the adjusted self-efficacy level.

For example, using clinical guidelines, it can be determined that a patient's lab test results are not in a good range and that the patient may need to do something to improve it. These improvement instruments may be categorized into different instrument catalogs. For instance, two catalogs may be identified for which an improvement may be suggested to the patient, e.g., healthier diet and being more active. From the patient's literacy score, it can also be determined that the patient is more willing or ready to doing exercise. The methodology and/or system of the present disclosure in one embodiment may then generate more instructions regarding to doing exercises in the care plan of the patient.

Based on the dynamically identified instruments as described above with reference to FIG. 1, customization points in care plans may be identified and clinical decision support at the point of care may be provided. Customization points in patient engagement plans are identified, for example, after care team B provides health coaching and medical care to patient A, by the system that monitors the gradual accretion of relevant health knowledge or any changes in the patient self-efficacy level through patients' responses to help dynamically adjust suitable subsequent assessment items, suggest next engagement intervention, and provide alerts/reminders to care providers to review patient case and customize engagement plans. For example, if patient A suddenly gave up self-management due to perceived obstacles, education materials on the relevant problem solving and coping strategy may be presented to them.

Care provider team often includes more than one clinician, and if any provider makes any changes in assessment, engagement intervention, or engagement plan, the system notifies and coordinates referrals, follow-ups, and treatment appointments with other care team members. Such changes are identified as customization points in care plan templates for providers/payers/policy makers' reference in one embodiment.

Clinical decision support may be provided at the point of care. The system can visualize a patient self-efficacy map (e.g., as shown in FIG. 2) based on risk stratification, prediction model, medical evidence, and institutional protocols to assist care team B with their clinical decision making.

Following the care process, the system in one embodiment also presents patient A's situation insight such as the observed changes of self-efficacy level over time along with clinical parameters compared to baseline medical results, primary risk factors identified, and personalized care management suggestion to clinicians at the right steps so that they can revise coaching and even treatment plans accordingly.

In one embodiment, system components and analytics may be provided for dynamic instrument composition. In one aspect, the analytics method of the present disclosure may utilize an approach similar to those used in the field of computer-adaptive testing (CAT) for subject classification. In the present disclosure, however, the approach in one embodiment selects the available items to discriminate patients' self-efficacy, and the categories vary from dimensions to dimensions and can be more than two.

Figure 2:
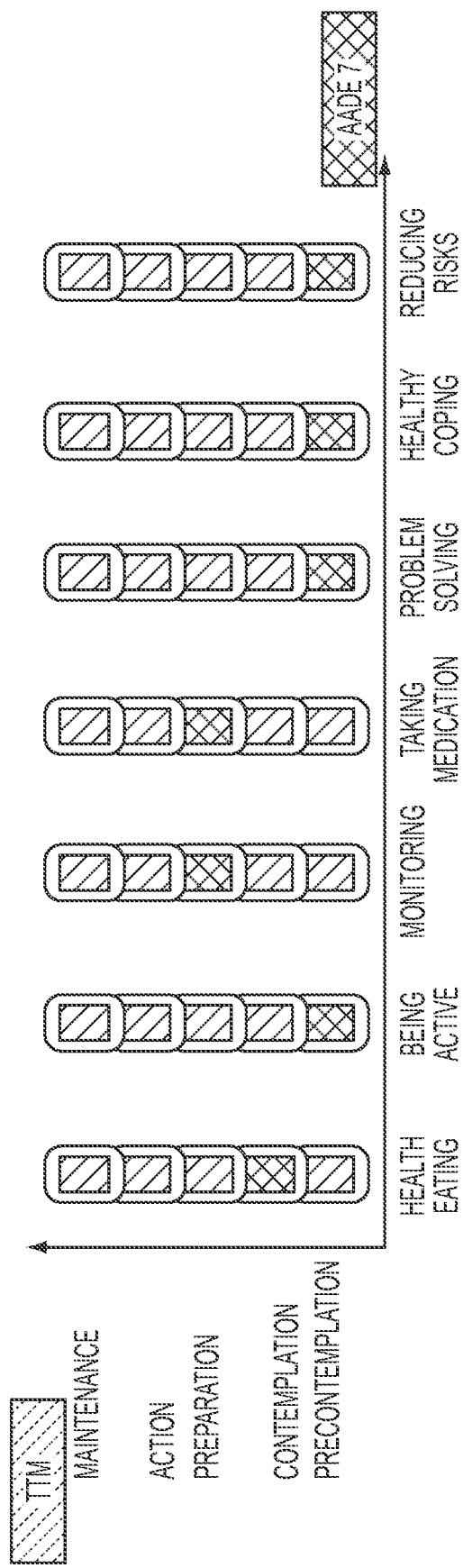
FIG. 2 is an example map showing patient self-efficacy estimation, for example, produced by a methodology of the present disclosure.

FIG. 2 is an example map showing patient self-efficacy classification estimation, for example, produced by a methodology of the present disclosure. The x-axis refers to seven self-management care dimensions; the y-axis refers to the five stages of change in the Trans-theoretical model of health behavior change (TTM) model. Such map may be dynamically generated based on the methodology's assessment, for example, and show changes or progress of the patient in self-efficacy, for example, via a user interface on a computer screen. For instance, the literacy application (shown in FIG. 1) may present such user interface map.

FIG. 2, as a simple example, shows the five TTM stages of changes adopted in the present disclosure in one embodiment as the categories for each of the seven AADE DM care dimensions. Every patient will receive a set of items tuned for classification purposes. Different from the CAT for classification approach that selects items from all content areas to ensure coverage, the system of the present disclosure in one embodiment pro-actively selects the dimension with the most surprising change to work on first.

In the example shown in FIG. 2, assessment items are categorized into seven dimensions, each being developed to measure a quantity of interest, e.g., literacy level in healthy eating, and modeled with its own parameters such as difficulty. Patients are also modeled with a set of parameters including both clinical and non-clinical ones. In the model development stage, for the seven dimensions of interest, a pool of items and responses are modeled to link the response variables (either dichotomous or polytomous) to a multitude of latent trait variables. Patients' previous responses are used to tailor the selection of items for each patient, based on the latent trait of self-efficacy found within each of the seven dimensions. In particular, the system models the temporal dependency of patient self-efficacy to dynamically select the most important dimension to be educated next and those items that fit user's current level (as represented with a single measurement in each dimension). Using this methodology, patients are presented with a dynamically composed instrument for assessment in their associated context, and fewer questions are needed to achieve a similar level of measurement accuracy.

Figure 3:
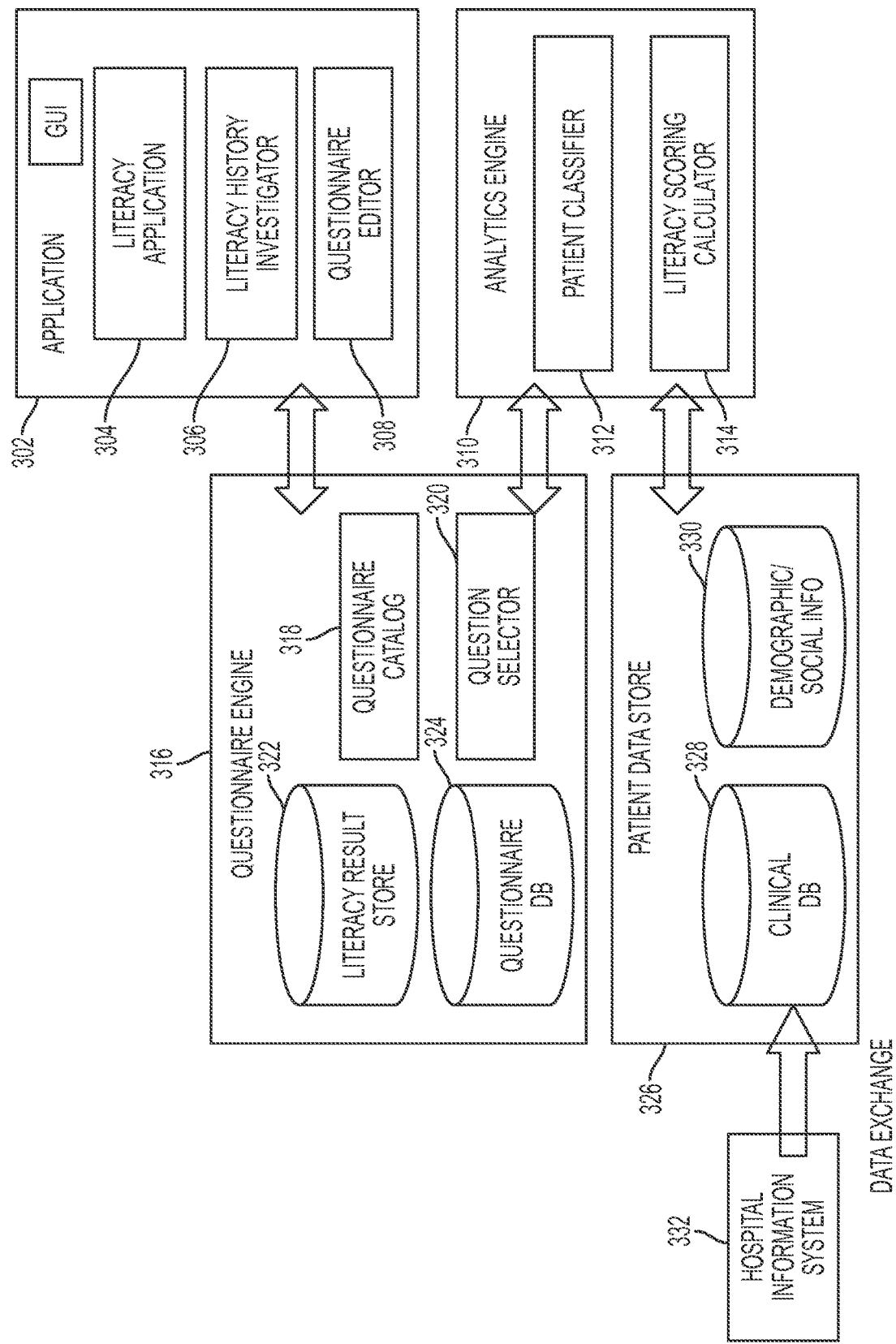
FIG. 3 is a diagram showing components of a system that provides a dynamic and accretive composition of patient engagement instruments for personalized plan generation in one embodiment of the present disclosure.

FIG. 3 is a diagram showing components of a system that provides a dynamic and accretive composition of patient engagement instruments for personalized plan generation in one embodiment of the present disclosure. An application 302 may be implemented as a mobile application or a web application or another computer executable application and allows users of the application to educate an individual patient in managing their health. The application in one embodiment invokes an analytics engine 312 and a questionnaire engine 316, or the like functionalities. The application 302 may include a literacy application component 304 that presents a set of questions to a patient and/or receive responses or answers. The literacy application component 304 may also present a set of instrument items to the patient. The application 302 may also include a literacy history investigator component 306 that allows a user to determine how a patient's literacy or self-efficacy changes over time. A user interface associate with the application 302 may present the determined self-efficacy changes. The application 302 may also include a questionnaire editor 308 that allows a user to add and delete questions from a questionnaire catalog 318 for presenting to a patient. A question can be deleted if it has already been answered by a patient to the case manager's satisfaction, or in the case that the patient has achieved more advanced knowledge about care management, a question that is too easy for a patient to answer can be deleted. In one aspect, the question itself is not deleted from the question database; rather, it is removed or excluded from a questionnaire that is presented to a particular patient. A question editing function provided by the question editor 308 allows for domain experts (or another) to maintain the question database to keep them as effective as possible.

A questionnaire engine 316 may include a questionnaire database 324 comprising questions regarding health management that may be presented to a patient. For example, a question selector 320 may select questions in the questionnaire catalog 318. The questionnaire engine 316 further may include a literacy result store that stores literacy or self-efficacy results, e.g., computed by an analytics engine 310. For instance, the questionnaire engine 316 may select a set of initial instrument items associated with an initially determined level of self-efficacy based on the care dimension category classified by the analytics engine. Further, the questionnaire engine 316 may select a next set of instrument items associated with another level of self-efficacy determined based on the analytics engine's literacy score calculation.

Example interaction among the components in FIG. 3 is illustrated as follows. When a new patient comes in, a case manager may utilize the graphic user interface to launch the literacy application 302. The system of the present disclosure in one embodiment activates the questionnaire editor 308, which communicates with the questionnaire selector 320 to retrieve the initial assessment questions from the questionnaire database 324 according to the right questionnaire catalog 318. To decide which questionnaire catalog is right for the patient, the system may activate the analytics engine 310 to retrieve the patient's clinical information such as basic demographic information 330, social and family history 330, medical history 328 or diagnosis 328 from patient data store 326 based on hospital information system's input 332. The analytics engine 310 may then assign a patient classifier 312 to capture the above patient-specific characteristics. Once the patient completes the initial assessment questionnaire, the analytics engine 310 may calculate a literacy score 314 that reflects how well the patient understands his/her conditions and the level of knowledge on care management. This score as well as the actual questionnaire answers are stored as the literacy results 322 by the questionnaire engine 316. When the patient comes back for a follow up, the literacy history investigator 306 may communicate with the questionnaire engine 316 to look up historical literacy result scores 322, and trigger the questionnaire editor 308 to work with question selector 320 again to tailor the next round of assessment with the most suitable questions.

An analytics engine may include a patient classifier component 312 and a literacy scoring calculator component 314. The analytics engine may receive patient answers that are input via the literacy application 304, and also may retrieve patient data from a patient data store 326 that may include a clinical database 328 and patient demographic and/or social information 330. The patient data store 326 may be obtained via a hospital information system 332. In another aspect, the patient data store 326 may be connected to a hospital information system 332.

Based on the patient data and/or answers received by the literacy application 304, the analytics engine 312 may classify a patient into a classification category. For example, the analytics engine's classifier 312 may classify the patient's condition based on the patient's data into a care dimension category. Using the patient classification and the patient data obtained from the patient data store 326, the analytics engine 310 (e.g., a literacy scoring calculator component 314 of the analytics engine) determines a literacy score, also referred to as a self-efficacy measure or measurement for the patient. The patient data may also include medical results of lab tests performed associated with the patient, which information may be also used in determining the literacy score. For instance, the patient's answers or responses and the patient data are synthesized and analyzed for determining the literacy score or self-efficacy measure.

The self-efficacy measurement of the patient may be stored in the literacy result store 322. Based on the self-efficacy measurement computed by the analytics engine 310 and/or stored in the literacy result store 322, the question selector 320 selects appropriate level of questions from the questionnaire database 324 for the patient. The literacy application 304 may present the selected questions to the patient.

The components shown in FIG. 3, e.g., the application 302, the questionnaire engine 316 and the analytics engine 310 are computer executable components that run on one or more hardware processors. The data store such as the literacy result store 322, the questionnaire database 324, and patient data store 326 may be stored on a physical storage device or memory device.

The processing described above in one embodiment is performed for multiple patients, each patient having his or her own self-efficacy measurement. As the patient answers the selected questions, the patient's self-efficacy measurement may be further updated by the analytics engine computing the score based on the those answers.

The methodology of the present disclosure in one embodiment is progressive in that the method can assist in the gradual increase of test difficulty during the selection process so as to enable the composition of a succinct personalized instrument for each individual patient. The methodology of the present disclosure in one embodiment is proactive in that the method can help healthcare professionals focus or zero in onto specific dimensions each individual patient is in need of improvement. The methodology of the present disclosure in one embodiment is adaptive in that the method adapts to not only the latent traits of individual patients, but also the context of patient engagement. The methodology of the present disclosure in one embodiment is flexible in that the method can be tuned to suit the needed accuracy of measurement required by healthcare professionals according to the care need. For patients of critical need, the required accuracy of self-efficacy measurement can be tuned higher.

In one embodiment, the system and methodology may model not only the latent trait of patient self-efficacy as the one-shot understanding approach, but also the temporal dynamics across concurrent assessments. Specifically, the system and methodology in one embodiment employ information of both the dimension of self-efficacy and prior distributions that result in dynamic linear models for the latent traits of patient self-efficacy and assessment item parameters. The responses over time, assessment items, and patient characteristics are modeled with a patient's self-efficacy level, a difficulty parameter, a discriminability parameter, and a coefficient vector that estimates the average measurement at the specified time point in each dimension. The prior of the dynamic self-efficacy levels is first estimated with the baseline results of each patient; in addition, an evolution variance parameter is included to indicate the dependency among self-efficacy levels obtained at different time points. Then, the posterior density of the model parameters are obtained by timing the prior density with the sampling density.

In one embodiment, Markov Chain Monte Carlo (MCMC) algorithms are used to fit the model, and the posterior density of the self-efficacy of each patient can be plotted. Surprising level of the changes in each dimension can be calculated using a sliding window approach to determine what dimension to address between and during clinical encounters and which assessment items to select in the next round. The posterior density of the self-efficacy level of each dimension can also be plotted to understand the overall quality of health education in the different dimensions and use that information to fine-tune the patient engagement plans.

Effective patient engagement may demand short, yet valid measurement of self-efficacy. The inferred knowledge of patients can then be used to select iteratively what is the most important dimension to be tested and educated next, and at which level of difficulty to set the test item and education material. The dynamically and accretively composed instrument may be an assessment kit that includes the most critical test items and education materials. Having established such instruments, healthcare professionals can use them to compose a shorter assessment without compromising the precision of measurement. In addition, the dynamicity information, which reflects the surprise level of the temporal change in the quantity of interest in the different care dimensions, can help identify key customization points in each respondent's engagement plan. The differentiating feature of the newly developed dynamic approach is expected to guide patients through their self-management reinforcement cycles, while tightly integrated into clinical workflow and standard care processes.

In one aspect, the system and/or methodology of the present disclosure may be integrated with electronic kiosks at point of service to obtain critical patient feedbacks. The system and methodology measure self-efficacy, and also provide explanations on how the patient contexts and assessments interact. This, for example, is important to the post-hoc analysis of population sub-grouping for dynamic categorization.

Figure 4:
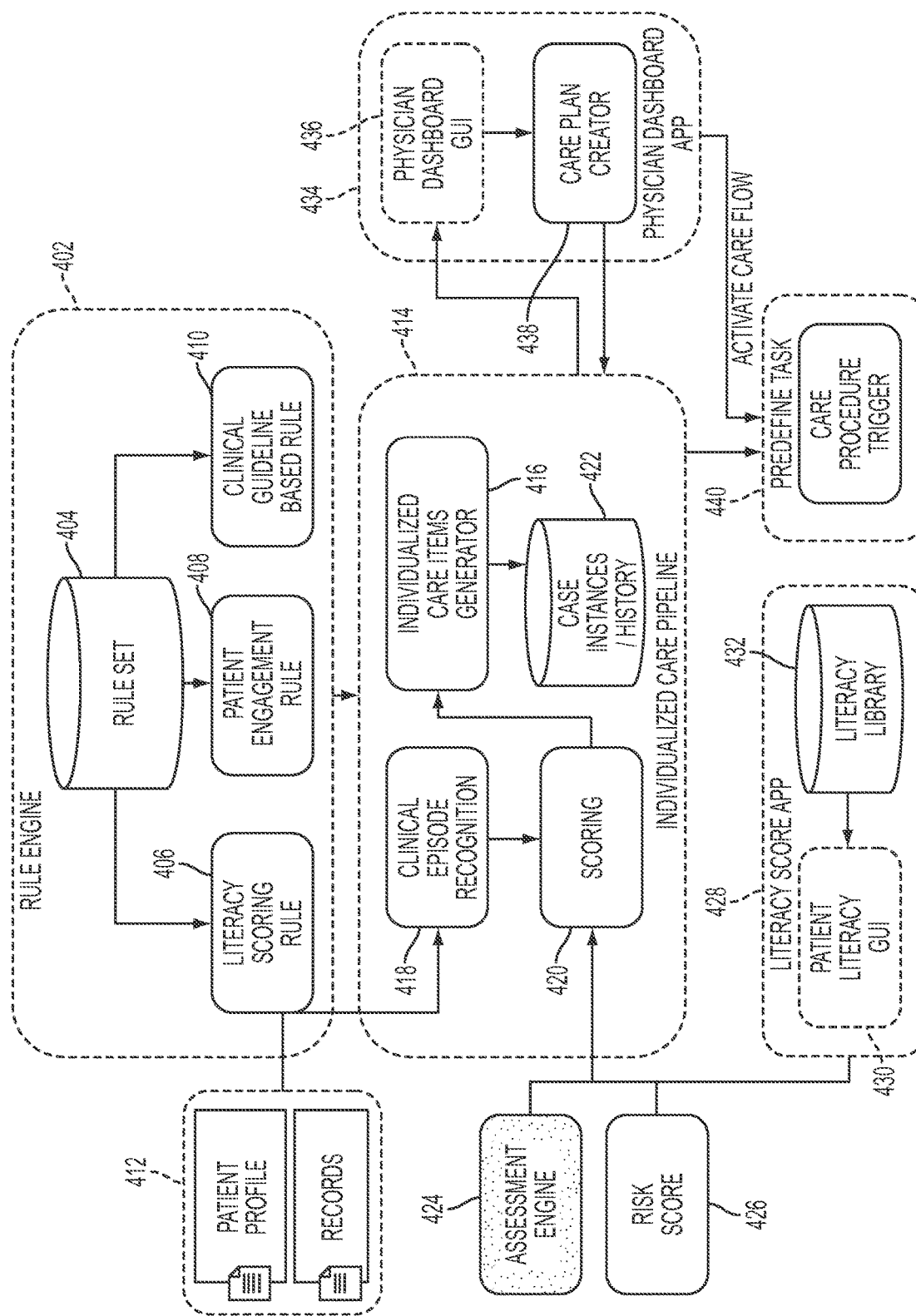
FIG. 4 is a diagram illustrating components for patient engagement that utilizes patient literacy application of the present disclosure in one embodiment.

FIG. 4 is a diagram illustrating components for patient engagement that utilizes patient literacy application of the present disclosure in one embodiment. A rule engine 402 may include a rule set database 404 that comprises literacy scoring rule 406, patient engagement rule 408 and clinical guideline based rule 410. The patient engagement rule 408 may include instructions or rules regarding how to interact with a patient. The clinical guideline based rule 410 may include disease care guidelines. The literacy scoring rule 406 may include dynamic information about patients, e.g., obtained from a patient profile and other records 412.

Individualized care pipeline 414 may include an individualized care items generator 416 that generate a customized care plan for a specific individual patient based on clinical episode recognition 418 and reassessed score 420 of the patient's self-efficacy measurement. The individualized care items or plans may be stored in a database 422.

For instance, a plurality of reassessment or rescoring engines 424, 426 determine a self-efficacy measurement associated with the individual patient, for example, using a literacy score application 428, which may include a patient literacy graphical user interface (GUI) 430 and literacy library 432. The literacy score application 428 may include the components shown in FIG. 3.

A dashboard application 434 may include a dashboard graphical user interface (GUI) 436 that may present the individualized care items generated at 414, for example, to a user using the application, e.g., a health care giver such as a physician. A user may create a care plan based on the individualized care items. For example, the user may select the individualized care items via the GUI 436, and a care plan creator 438 creates a plan based on the input by the user on the GUI 326.

Based on the care plan created by the care plan creator 438, a care flow may be activated. For example, the defined tasks in the care plan are triggered or activated as shown at 440.

Figure 5:
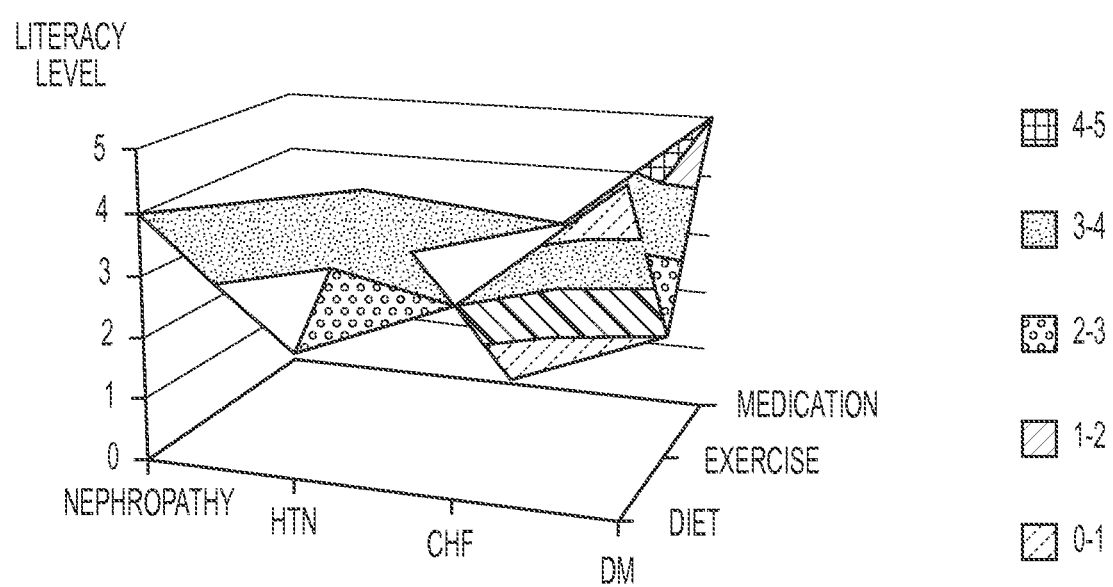
FIG. 5 is a diagram illustrating data associated with a patient exposed to a multitude of co-morbid conditions having different literacy levels across the three different care dimensions (medication, exercise, diet), indicating an individual need in the engagement plans.

FIG. 5 is a multi-dimensional diagram illustrating a patient exposed to a multitude of co-morbid conditions having different literacy levels across the three different care management interventions (medication, exercise, diet) in the treatment dimension, indicating an individual need in the engagement plans. The disease dimension of the diagram shows co-morbid conditions of hyptertension (HTN), congestive heart failure (CHF), and Diabetes Mellitus (DM) as an example. In the present disclosure in one embodiment, patient engagement strategies may be progressively tailored by dynamic categorization and care plan generation. Progressive or iterative reinforcement cycles may be provided within or across categories based on a patient's readiness, for example, with respect to capability and motivation. As the patient's condition become more complicated, more co-morbidities can be added to the disease dimension. Similarly, more care management interventions can be added to the treatment dimension.

In one aspect, a progressive tailoring of the present disclosure enables uses cases such as providing a service model for evidence generation, e.g., question-answer data analytics for providing insights for individual's needs, and easier access to measure patient engagement and satisfaction.

As described above, a system and methodology of the present disclosure may dynamically choose the most appropriate instrument for customized patient engagement, e.g., based on a patient's latent adherence trait estimated from lifestyle and other clinical data. In addition the system and methodology of the present disclosure may identify customization points in care plans, e.g., monitor the accumulative change in the patient's health literacy level. Further, the system and methodology of the present disclosure may provide clinical decision support at the point of care, e.g., adjust patient engagement strategies and allocate resources accordingly.

Figure 6:
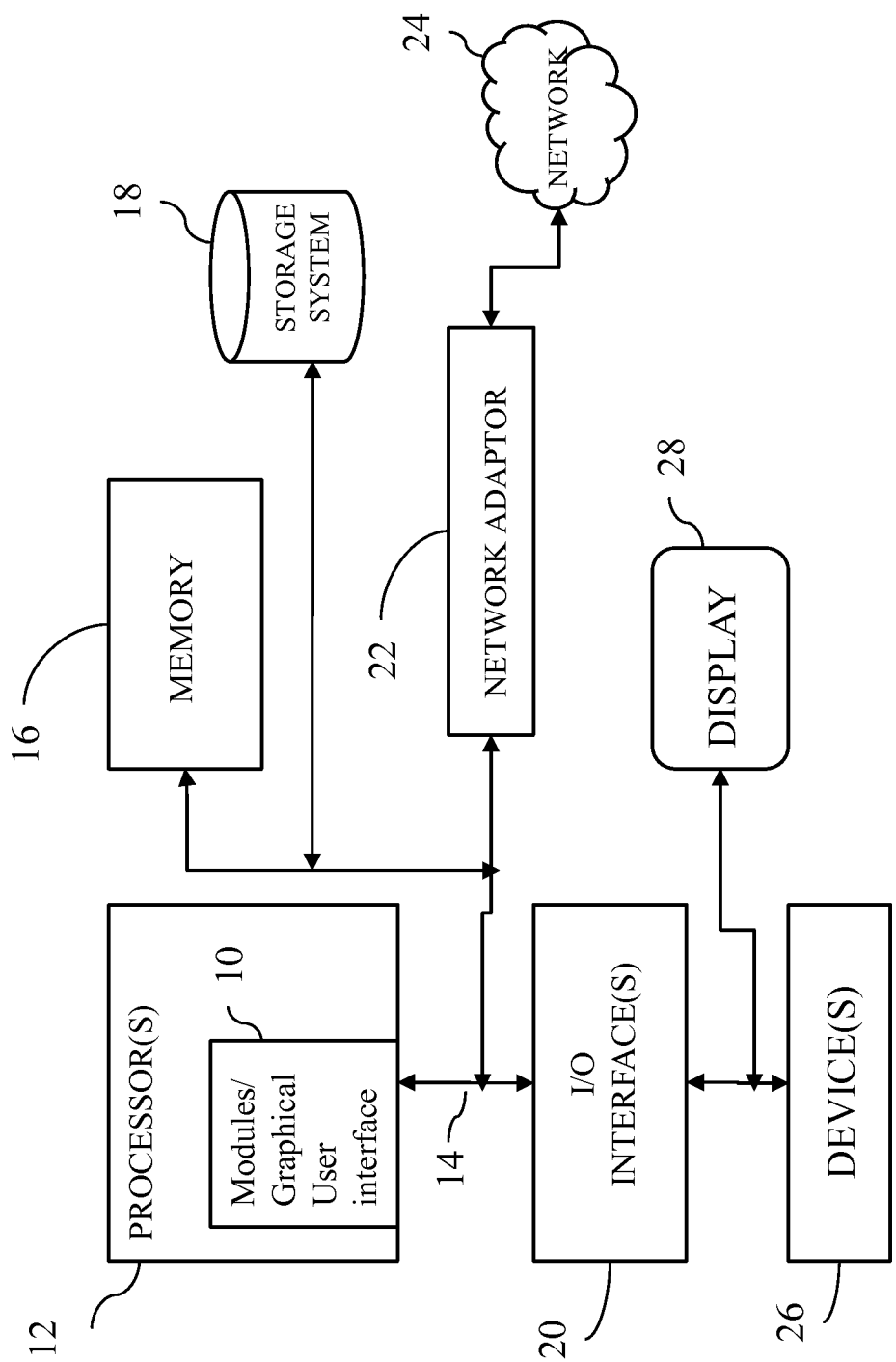
FIG. 6 illustrates a schematic of an example computer or processing system that may implement one or more components of system that dynamically and accretively composes patient engagement instruments for individualized plan generation in one embodiment of the present disclosure.

FIG. 6 illustrates a schematic of an example computer or processing system that may implement one or more components of system that dynamically and accretively composes patient engagement instruments for individualized plan generation in one embodiment of the present disclosure. The computer system is only one example of a suitable processing system and is not intended to suggest any limitation as to the scope of use or functionality of embodiments of the methodology described herein. The processing system shown may be operational with numerous other general purpose or special purpose computing system environments or configurations. Examples of well-known computing systems, environments, and/or configurations that may be suitable for use with the processing system shown in FIG. 6 may include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The computer system may be described in the general context of computer system executable instructions, such as program modules, being executed by a computer system. Generally, program modules may include routines, programs, objects, components, logic, data structures, and so on that perform particular tasks or implement particular abstract data types. The computer system may be practiced in distributed cloud computing environments where tasks are performed by remote processing devices that are linked through a communications network. In a distributed cloud computing environment, program modules may be located in both local and remote computer system storage media including memory storage devices.

The components of computer system may include, but are not limited to, one or more processors or processing units 12, a system memory 16, and a bus 14 that couples various system components including system memory 16 to processor 12. The processor 12 may include a module 10 that performs the methods described herein. The module 10 may be programmed into the integrated circuits of the processor 12, or loaded from memory 16, storage device 18, or network 24 or combinations thereof.

Bus 14 may represent one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system may include a variety of computer system readable media. Such media may be any available media that is accessible by computer system, and it may include both volatile and non-volatile media, removable and non-removable media.

System memory 16 can include computer system readable media in the form of volatile memory, such as random access memory (RAM) and/or cache memory or others. Computer system may further include other removable/non-removable, volatile/non-volatile computer system storage media. By way of example only, storage system 18 can be provided for reading from and writing to a non-removable, non-volatile magnetic media (e.g., a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 14 by one or more data media interfaces.

Computer system may also communicate with one or more external devices 26 such as a keyboard, a pointing device, a display 28, etc.; one or more devices that enable a user to interact with computer system; and/or any devices (e.g., network card, modem, etc.) that enable computer system to communicate with one or more other computing devices. Such communication can occur via Input/Output (I/O) interfaces 20.

Still yet, computer system can communicate with one or more networks 24 such as a local area network (LAN), a general wide area network (WAN), and/or a public network (e.g., the Internet) via network adapter 22. As depicted, network adapter 22 communicates with the other components of computer system via bus 14. It should be understood that although not shown, other hardware and/or software components could be used in conjunction with computer system. Examples include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements, if any, in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

We claim:

1. A system of selecting patient engagement instruments for individualized care, comprising:
   one or more hardware processors;
   an analytics engine operable to execute on one or more of the hardware processors, the analytics engine further operable to retrieve a patient's data from a patient database stored in a memory device, the patient database connected to a hospital information system, the analytics engine further operable to classify the patient's condition based on the patient's data into a care dimension category; and
   a questionnaire engine operable to execute on one or more of the hardware processors, the questionnaire engine further operable to select a set of initial instrument items associated with an initially determined level of self-efficacy based on the care dimension category classified by the analytics engine;
   a literacy application module operable to execute on the one or more hardware processor and further operable to invoke the analytics engine and the questionnaire engine, and further operable to receive responses associated with the one or more initial instrument items from the patient, the analytics engine further operable to receive medical results of lab tests performed associated with the patient, the analytics engine further operable to synthesize and analyze the responses and the medical results, the analytics engine further operable to determine a self-efficacy measure associated with the patient based on the synthesizing and the analyzing, the self-efficacy measure representing how well the patient understands the patient's conditions and the patient's level of knowledge on care management along one of a plurality of care dimensions comprising healthy diet, being active, monitoring, taking medication, problem solving, healthy coping and reducing risks, wherein the self-efficacy measure represents a patient's literacy score per dimension of care, and wherein based on the self-efficacy measure, the analytics engine further determines a dimension from the plurality of care dimensions to test and educate the patient, the analytics engine further operable to adjust the initially determined level of self-efficacy to another level according to the self-efficacy measure, the questionnaire engine further operable to select a next set of instrument items associated with said another level, said another level used to select a difficulty level and the next set of instrument items correspond to the difficulty level, the literacy application module further operable to present the next set of instrument items to the patient, wherein the next set of instrument items comprising questionnaires and health education material are dynamically composed corresponding to said another level, reducing redundancy of presenting instrument items currently inapplicable to the patient based on dynamic changes in patient's self-efficacy measure, wherein the analytics engine is operable to run a batch computer process to dynamically estimate a current self-efficacy level iteratively while the literacy application module is operable to present the next set of instrument items iteratively, estimating the current self-efficacy levels including at least modeling responses over time, assessment items and patient characteristics with the level of self-efficacy, the modeling including an evolution variance parameter which indicates a dependency among self-efficacy levels obtained at different time points, wherein the literacy application module is further operable to present a multi-dimensional graphical view including at least a 3-dimensional display view including x-y-z axes representing a multitude of co-morbid conditions in a first dimension, different literacy levels in a second dimension, across different care management interventions in a third dimension, the graphical view updated dynamically based on the dynamic changes in the patient's self-efficacy measure, the literacy application module running as a mobile application and communicating with the analytics engine and the questionnaire engine in providing the next set of instrument items, the literacy application being integrated with the hospital information system and a kiosk at a point of service to at least dynamically determine the care dimension category in selecting the next set of instrument items, wherein at least one of the hardware processors determines surprising levels of changes in each dimension of care using a sliding window in a fitted model showing a posterior density of the patient's self-efficacy measure, the surprising levels of the changes allowing for dynamically determining the care dimension category for selecting the next set of instrument items, wherein a care plan is created at least based on the patient's self-efficacy measure, wherein creating of the care plan triggers via the literacy application an activation of a task in the care plan, wherein the multi-dimensional graphical view is generated and updated based on dynamic categorization and care plan generation.

2. The system of claim 1, wherein the set of initial instrument items and the next set of instrument items comprise questions and educational guidelines associated with managing heath of the patient.

3. The system of claim 1, wherein based on the patient's responses to the next set of instrument items, the analytics engine repeats synthesizing and analyzing, determines an updated self-efficacy measure, and adjusts the level of self-efficacy according to the updated self-efficacy measure, wherein the questionnaire engine selects another set of instrument items based on the adjusted level of self-efficacy and the literacy application module presents said another set of instrument items.

4. The system of claim 3, wherein the literacy application module comprises a graphical user interface operable to notify a care team of a change in the level of self-efficacy.

5. The system of claim 4, wherein the graphical user interface presents observed changes based on the patient's responses to the next set of instrument items and the initial set of instrument items, wherein a treatment plan for the patient is revised based on the observed changes.

6. The system of claim 5, wherein the observed changes are presented with clinical parameters associated with the patient received from the hospital information system.

7. The system of claim 1, wherein the method is performed for a patient receiving health coaching and medical care from a given facility.

8. A computer program product comprising a computer readable storage medium having program instructions embodied therewith, wherein the computer readable storage medium is not a transitory signal per se, the program instructions readable by a processor to cause the processor to perform a method comprising:

retrieving patient data associated with a patient from a patient database stored in a memory device, the patient database connected to a hospital information system;

classifying a condition of the patient based on the patient data into a care dimension category;

selecting a set of initial instrument items associated with an initially determined level of self-efficacy based on the classifying;

receiving from a mobile application responses associated with the one or more initial instrument items of the patient;

receiving medical results of lab tests performed associated with the patient;

synthesizing and analyzing the responses and the medical results;

determining a self-efficacy measure associated with the patient based on the synthesizing and the analyzing, the self-efficacy measure representing how well the patient understands the patient's conditions and the patient's level of knowledge on care management along one of a plurality of care dimensions comprising healthy diet, being active, monitoring, taking medication, problem solving, healthy coping and reducing risks, wherein the self-efficacy measure represents a patient's literacy score per dimension of care and wherein based on the self-efficacy measure, the a dimension from the plurality of care dimensions to test and educate the patient is determined;

adjusting the initially determined level of self-efficacy to another level according to the self-efficacy measure, the adjusting performed by a computer-implemented batch process;

selecting a next set of instrument items associated with said another level communicated from the computer-implemented batch process, said another level used to select a difficulty level and the next set of instrument items correspond to the difficulty level; and presenting the next set of instrument items to the patient via a graphical user interface, wherein the next set of instrument items comprising questionnaires and health education material are dynamically composed corresponding to said another level, reducing redundancy of presenting instrument items currently inapplicable to the patient based on dynamic changes in patient's self-efficacy measure, wherein the synthesizing and analyzing is invoked automatically as the computer-implemented batch process to dynamically estimate a current self-efficacy level iteratively, estimating the current self-efficacy levels including at least modeling responses over time, assessment items and patient characteristics with the level of self-efficacy, the modeling including an evolution variance parameter which indicates a dependency among self-efficacy levels obtained at different time points, wherein the method further includes causing presenting of a multi-dimensional graphical view including at least a 3-dimensional display view including x-y-z axes representing a multitude of co-morbid conditions in a first dimension, different literacy levels in a second dimension, across different care management interventions in a third dimension, the graphical view updated dynamically based on the dynamic changes in the patient's self-efficacy measure, the computer-implemented batch process communicating with the mobile application in providing the next set of instrument items, the mobile application being integrated with the hospital information system and a kiosk at a point of service to at least dynamically determine the care dimension category in selecting the next set of instrument items, wherein the processor is caused to determine surprising levels of changes in each dimension of care using a sliding window in a fitted model showing a posterior density of the patient's self-efficacy measure, the surprising levels of the changes allowing for dynamically determining the care dimension category for selecting the next set of instrument items, wherein a care plan is created at least based on the patient's self-efficacy measure, wherein creating of the care plan triggers via the mobile application an activation of a task in the care plan, wherein the multi-dimensional graphical view is generated and updated based on dynamic categorization and care plan generation.

9. The computer program product of claim 8, wherein the set of initial instrument items and the next set of instrument items comprise questions and educational guidelines associated with managing heath of the patient.

10. The computer program product of claim 8, further comprising:

based on the patient's responses to the next set of instrument items, repeating the synthesizing and analyzing, the determining a self-efficacy measure, the adjusting, the selecting a next set of instrument items and the presenting the next set of instrument items, wherein the adjusting comprises adjusting a currently determined level to a next level of self-efficacy.

11. The computer program product of claim 10, further comprising:

notifying a care team of a change in a self-efficacy level based on the adjusting the currently determined level to the next level of self-efficacy.

12. The computer program product of claim 10, further comprising:

presenting observed changes based on the patient's responses to the next set of instrument items and the initial set of instrument items, wherein a treatment plan for the patient is revised based on the observed changes.

13. The computer program product of claim 12, wherein the observed changes are presented with clinical parameters associated with the patient received from the hospital information system.

* * * * *